United States Patent [19]

Schmid

[11] 4,300,899
[45] Nov. 17, 1981

[54] TRIAZINE AND PYRIMIDINE DERIVATIVES AS RESERVING AGENTS

[75] Inventor: Hans-Rudolf Schmid, Riehen, Switzerland

[73] Assignee: Sandoz Ltd., Basel, Switzerland

[21] Appl. No.: 123,084

[22] Filed: Feb. 20, 1980

Related U.S. Application Data

[63] Continuation of Ser. No. 921,552, Jul. 3, 1978, abandoned.

[30] Foreign Application Priority Data

Jul. 7, 1977 [CH] Switzerland ............ 8423/77
Jul. 7, 1977 [CH] Switzerland ............ 8424/77

[51] Int. Cl.³ .............................. D06P 5/12
[52] U.S. Cl. .............................. 8/455; 8/540; 8/566; 8/590; 8/917; 8/924; 8/927; 8/928; 544/211
[58] Field of Search ............ 8/455, 566, 567, 917, 8/924, 927, 928, 540, 590

[56] References Cited

U.S. PATENT DOCUMENTS 3,743,477  7/1973  Egli et al. .................. 8/448
3,775,045 11/1973  Buehler et al. .............. 8/448
3,926,548 12/1975  Moriyama et al. ........... 8/115
3,947,374  3/1976  Loffelman et al. .......... 252/99

FOREIGN PATENT DOCUMENTS 759976   5/1971 Belgium .
838337   6/1960 United Kingdom .
1410552 10/1975 United Kingdom .

Primary Examiner—A. Lionel Clingman
Attorney, Agent, or Firm—Gerald D. Sharkin; Richard E. Vila; Thomas C. Doyle

[57] ABSTRACT

The present invention relates to compounds of formula $I_x$,

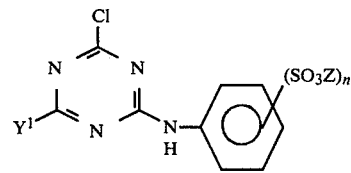

in which $Y_1$ is $(C_{1-6})$ alkoxy,
Z is hydrogen, alkali metal or ammonium, and
n is 1 or 2 and a process for treating anionic dyeable substrates therewith to reserve the same against anionic dyes.

19 Claims, No Drawings

TRIAZINE AND PYRIMIDINE DERIVATIVES AS RESERVING AGENTS

This is a continuation of application Ser. No. 921,552 filed July 3, 1978 and now abandoned.

The present invention relates to a process for treating anionic dyeable substrates with a reserve agent. More particularly the present invention relates to a process for treating such substrates with a reserve agent so as to achieve a 'space dye' effect with dyed or printed substrates.

Accordingly, the present invention provides a process for treating anionic dyeable substrates to reserve the same against anionic dyes comprising applying to the substrate a compound of formula I,

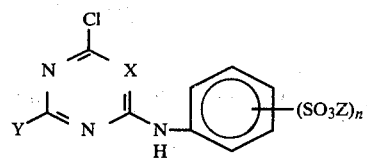

wherein either X is —N= and Y is $(C_{1-6})$alkoxy or X is

and Y is chlorine,
Z is hydrogen, an alkali metal or ammonium,
and n is 1 or 2,
followed by fixation.

Preferred compounds of formula I are those where X is —N= and Y is isopropoxy or X is

and Y is Cl, especially those wherein n is 1, with the sodium salts being the most preferred.

The compounds of formula I wherein X is —N= and Y is $(C_{1-6})$ alkoxy are new and form part of the present invention. Such compounds may be prepared by reacting a compound of formula II,

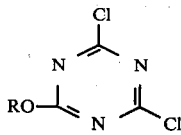

with a compound of formula III,

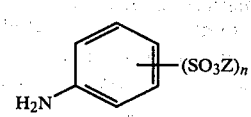

in alkaline medium in accordance with known methods. If it is wished to obtain a compound of formula I wherein Z is hydrogen, the salt form may be converted to the free acid form in accordance with known methods. The compounds of formula I may be isolated in accordance with known methods e.g. by precipitation, the slurry of the compound of formula I may be used as such or may be filtered and obtained as a press-cake.

The compounds of formula I may be applied to the substrate by known methods, for example by padding or printing local areas thereof or by treating the substrate in a bath containing a compound of formula I, e.g. by the exhaust method. In order to achieve a space dye effect substrates to which a compound of formula I has been applied by the exhaust method are subsequently combined e.g. by twisting or blending with untreated substrate prior to dyeing or printing the whole.

The compounds of formula I may be made up into padding liquors or printing pastes in accordance with known methods, such pastes contain conventional additives such as thickeners etc.

The amount of compound of formula I in the paste or liquor can vary depending on the nature of the particular substrate, and the desired depth and/or contrast of the finally dyed substrate. Suitably pastes or liquors contain up to 150 g/kilogram, preferably from 5 to 50 g, more preferably from 10 to 40 g/kilogram.

When the compound of formula I is applied to the substrate by the exhaust method, the treatment bath suitably contains from 0.1 to 10%, preferably from 2 to 5% by weight of compound of formula I. The substrate is suitably treated for about one hour at 98° to 100° C.

Fixation of the compound of formula I on the printed or padded substrates may be effected by known methods, for example the compound may be fixed in a period of 50 hours in a moist atmosphere at room temperature, in a period of from 2 to 48 hours at a temperature of from 25° to 100° C. and in about 15 minutes at a temperature of from 95° to 130° C. Fixation of the compound of formula I on the substrate to which it has been applied by the exhaust process takes place in the bath.

Prior to or after fixation of a compound of formula I on the printed or padded substrate, a space dye effect is achieved by dyeing or printing the treated substrate in accordance with known methods.

Dyeing or printing the treated substrate with anionic dyes will result in the treated portions, depending on the amount of compound of I and on the dyestuff employed, remaining undyed or slightly dyed. Particularly marked reserve effects are achieved with anionic dyestuffs which contain at least two sulphonic acid groups, in fact full or almost full reservation of synthetic polyamide fibres is achieved with this type of dye. A step by step decrease in the degree of reservation is obtained with dyes bearing only one sulphonic acid group and with metal complex dyes. Dyes which contain fibre reactive groups, such as mono- and dichlorotriazine etc., which would cause them to be classified as reactive dyes are not embraced by the term "anionic dyes" as used herein.

Multi-colour effects may be obtained by dyeing or printing with a disperse dye and/or a basic dye in addition to an anionic dyestuff, whereby the disperse dye is not influenced by the reserve agent and the reserved portions are dyed in deep shades with the basic dyestuff. Dyeing with an anionic dye and disperse and/or basic dyestuff may be carried out in the same bath or may be carried out sequentially.

As will be appreciated the reserve agent and the dyestuff may be fixed in a single step. However, it is preferred to fix the compound of formula I before applying dyestuff to the substrate.

Suitable substrates dyeable with anionic dyes are filaments, fibres, yarns, woven, knitted and other non-woven fabrics comprising or consisting of natural polyamide, e.g. wool or silk; synthetic polyamide, e.g. nylon 6, 7, 11, 66, 76, 226, 610 and 6/66; basic modified polypropylene or basically modified polyacrylonitrile and acrylonitrile copolymers. Preferably, the substrate comprises a polyamide, most preferably a synthetic polyamide, e.g. nylon 6 or nylon 66.

In addition to the reservation of the substrate against anionic dyes, the treated portions of the substrate exhibit an improved dyeability with basic dyes. Furthermore, the compounds of formula I are less toxic than the reserve agents specifically disclosed in Swiss Pat. No. 525,997 whilst having the same, if not better, reserve capacity.

The following Examples further serve to illustrate the invention. In the Examples all parts are by weight and all temperatures are in degrees Centigrade unless otherwise stated.

EXAMPLE 1

Texturised nylon 66 carpet yarn is locally impregnated (100% weight increase of impregnated portions) with a paste containing
10 parts of a commercial Alginate Thickener
40 parts sodium carbonate (anhydrous)
680 parts water
9 parts octylphenyl-pentaglycolether
1 part anionic dispersing agent, e.g. modified sodium higher alkylsulphate
200 parts of a slurry containing 20% by weight of a compound of formula (a)

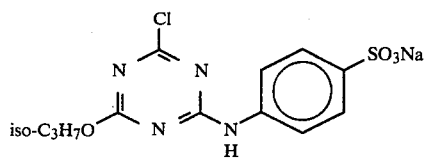

and 60 parts sodium dinaphthylmethanedisulphonate.

Homogeneity of the paste is achieved by vigorous stirring. The impregnated substrate is stored for 6 hours at room temperature (20°-25°) and then rinsed with cold water. The yarn is then tufted into a jute fabric. The thus obtained carpet is then exhaust dyed with a dye mixture of C.I. Disperse Yellow 3 and C.I. Acid Red 37 or C.I. Disperse Blue and C.I. Acid Red 37, whereby clear two colour dyeings are obtained.

If, instead of the above isopropoxy compound, the same amount of ethoxy-substituted- or butoxy-substituted-compound is employed a similar dyeing is obtained. A nylon 66 fabric is printed by the Vigoureux process (50% coverage with 100% weight increase of the printed portions) with a paste containing
30 parts Alginate thickener
40 parts sodium bicarbonate (anhydrous)
804 parts water
6 parts anionic dispersing agent, e.g. modified higher-alkylsulphate
30 parts of the compound of formula (a), and
90 parts sodium dinaphthylmethanedisulphonate.

Prior to application the paste is vigorously stirred until it is homogeneous. After printing, the fabric is treated in a saturated steam atmosphere for 10 minutes at 105° and then rinsed with cold water.

The fabric, thus locally reserved against anionic dyes, is cut into five equal parts and these are dyed, respectively, with the following dyes:
1% C.I. Acid Red 37 (2 sulphonic acid groups),
1% C.I. Acid Red 57 (1 sulphonic acid group),
1.5% C.I. Acid Red 216 (premetallized dye),
1% C.I. Disperse Red 43 (disperse dye),
1% C.I. Basic Red 44 (basic dye).

In all cases clear two tone dyeings are obtained.

If, instead of the compound of formula (a) the same amount of compound of formula (b)

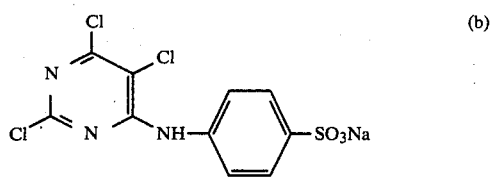

is employed, equally good results are obtained.

EXAMPLE 3

Carpet yarn of texturized nylon 66 fibre is impregnated at a 100% increase over the dry weight on the impregnated areas with a homogeneously stirred paste of the composition:
5 parts sodium Alginate thickener
30 parts anhydrous disodium phosphate
919 parts water
8 parts octylphenyl-pentaglycol ether
2 parts anionic dispersing agent, e.g. modified sodium higher alkylsulphate
9 parts of the compound of formula (b), and
27 parts of sodium dinaphthylmethanedisulphonate.

The impregnated yarn is stored at room temperature for one day and finally rinsed with warm and cold water.

The yarn is then tufted into a jute fabric and is exhaust dyed with a dyestuff mixture of C.I. Disperse Yellow 3 and C.I. Acid Blue 23. A clear two-colour dyeing is obtained.

EXAMPLE 4

A wool yarn is locally padded (100% weight increase on the impregnated areas) with a paste of the following composition:
5 parts Alginate thickener
3 parts phosphate buffer mixture, pH 9
885 parts water
24 parts octylphenyl-pentaglycol ether
6 parts anionic dispersing agent, e.g. modified higher alkylsulphate, and
45 parts of the compound of formula (a).

The paste is homogenized by vigorous stirring before application, and after padding the yarn is stored for 1 hour at room temperature, then rinsed with warm and cold water. The so treated material is exhaust dyed with a dyestuff mixture of C.I. Acid Blue 23 and C.I. Acid Yellow 25. A clear two tone dyeing is obtained.

EXAMPLE 5

Polypropylene yarn which has been chemically modified so as to be dyeable with anionic dyestuffs is locally impregnated with a paste of the following composition:
5 parts Alginate thickener
30 parts disodium phoshate
5 part trisodium phosphate 900 parts water
24 parts octylphenyl-pentaglycol ether
6 parts anionic dispersing agent, e.g. modified sodium higher alkylsulphate, and
30 parts of the compound of formula (b)

Prior to application the paste is stirred vigorously until homogeneous. The impregnated substrate is then steamed in a wet-steam atmosphere for 15 minutes at 100° and is subsequently rinsed with warm and cold water.

The so treated yarn is then exhaust dyed with C.I. Acid Orange 43 whereby the treated portions are weakly dyed and the untreated portions are dyed with a deep shade.

EXAMPLE 6

Modified polyacrylonitrile yarn is locally impregnated with a paste containing:
5 parts Alginate thickener
30 parts disodium phosphate
5 parts monosodium phosphate
400 parts water
24 parts octylphenyl-pentaglycol ether
6 parts anionic dispersing agent, e.g. modified sodium alkylsulphate, and
30 parts of the compound of formula (a).

Prior to application, homogeneity of the paste is achieved by vigorous stirring. The impregnated yarn is then treated in a saturated steam atmosphere at 110° and is subsequently dyed with C.I. Acid Orange 43 whereby the treated portions are noticeably lighter in depth than the untreated portions.

EXAMPLE 7

Texturized nylon 66 carpet yarn is put in a bath at 40° (liquor ratio 1:10) containing 5% of the compound of formula (a) and 5% monosodium phosphate. The bath is raised to the boil over a period of 30 minutes. After 1 hour at the boil the bath is emptied and the yarn is rinsed.

The so treated yarn is twisted together with untreated yarn, tufted into a jute fabric and exhaust dyed. The fabric is divided in two parts. One part is dyed with C.I. Disperse Yellow 3 and C.I. Acid Red 37 and the other part is dyed with C.I. Disperse Blue 3 and C.I. Acid Red 37. Two colour dyeings are obtained.

EXAMPLE 8

184 parts of cyanuric chloride are suspended in 467 parts of isopropanol. 106 parts of soda are then added and the temperature is raised slowly within 25 minutes to 40° C. After about 100-110 minutes when no free cyanuric chloride is left the reaction vessel is cooled to 0°-2° C. and 1000 parts of ice-water are added thereto. The pH at this stage should be ~9.3. Over the period of 60 minutes, 173 parts of sulfanilic acid are dissolved in 1000 parts of water and 133 g of a 30% NaOH solution are added. (The solution to be added should have a pH value of 5.5). The pH value during the addition of the above drops and is kept at 6.5-7 by adding further NaOH. After completion of the addition the mixture is heated over the period of about 2 hours to 50° C. and kept at this temperature for one further hour. (To keep the pH value at 6.5-7, approximately 40 parts of a 30% NaOH solution are necessary). After the addition of 11 parts sodium-monophosphate and 7.4 parts of disodium-phosphate (for buffering the solution at 6.5-7), a total amount of 900 parts (by volume) of an isopropanol/water mixture (88/12) are distilled off. After the addition of 250 parts of a NaCl and cooling to room temperature the reaction mixture is stirred for a further 20 minutes. The slurry obtained may be used as such to form padding liquors, printing paste or bath concentrate. The slurry has good storage stability.

If the mixture is filtered 700 parts of a moist press-cake, containing 56% of a dry product are obtained. The product contains approximately 15% of NaCl, it can be purified by recrystallisation; the free acid can be isolated by conventional means.

The product thus obtained is of formula (a) and can be used as such without further purification.

What is claimed is:

1. A process for reserving an anionic dyeable substrate against anionic dyes which comprises applying to the substrate a compound of formula I

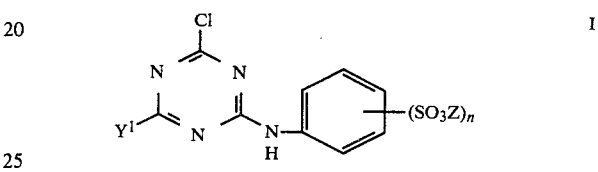

wherein Y is $(C_{1-6})$alkoxy,
Z is hydrogen, an alkali metal or ammonium,
and n is 1 or 2,
and then fixing said compound on said substrate.

2. A process according to claim 1 wherein n is 1.
3. A process according to claim 1 wherein n is 1.
4. A process according to claim 2 in which the treated substrate is dyed or printed with an anionic dyestuff before or after fixation of the compound of formula I.
5. A process according to claim 1, in which in compound of formula I, n is 1.
6. A process according to claim 1, in which in the compound of formula I, Y is iso-propoxy.
7. A process according to claim 6, in which in the compound of formula I, Z is alkali metal or ammonium and when n is 1, the sulpho group is in the para position.
8. A process according to claim 1, in which Z is sodium.
9. A process according to claim 1, in which the treated substrate is dyed or printed with an anionic dyestuff before or after fixation of the compound of formula I.
10. A process according to claim 9, in which the substrate is dyed or printed after fixation.
11. A process according to claim 9, in which the substrate is dyed or printed before fixation and fixation of the compound of formula I and of the dyestuff is effected in a single step.
12. A process according to claim 9, in which the substrate is dyed or printed with a disperse dyestuff and/or basic dyestuff in addition to an anionic dyestuff.
13. A process according to claim 7, in which the compound of formula I, is applied by padding, printing or by the exhaust method.
14. A process according to claim 13, in which the substrate is treated with a printing paste or padding liquor containing a compound of formula I in an amount of from 5 to 50 g per kilogram based on the total weight of the padding liquor or printing paste.
15. A process according to claim 9, in which the paste or padding liquor contains from 10 to 40 g per kilogram of a compound of formula I.

16. A process according to claim 1, in which the fabric is treated in a bath containing from 0.1 to 10% by weight of a compound of formula I.

17. A process according to claim 13, in which the padding liquor, printing paste or treatment bath contains from 0.1 to 5% of a weakly alkaline salt.

18. A process according to claim 1, in which the substrate comprises or consists of natural or synthetic polyamide, basic modified polypropylene or basically modified polyacrylonitrile and acrylonitrile copolymers.

19. A process according to claim 18, in which the substrate consists of or comprises polyamide.

* * * * *

UNITED STATES PATENT AND TRADEMARK OFFICE
CERTIFICATE OF CORRECTION

PATENT NO. : 4,300,899

DATED : November 17, 1981

INVENTOR(S) : Hans-Rudolf Schmid

It is certified that error appears in the above—identified patent and that said Letters Patent is hereby corrected as shown below:

Claim 1 in the formula; change "$Y^1$" to --Y--.

Claim 2 after "claim"; change "1" to --7--.

Claim 3 after "claim"; change "1" to --14--.

Signed and Sealed this

Twenty-fifth Day of May 1982

[SEAL]

Attest:

Attesting Officer

GERALD J. MOSSINGHOFF

Commissioner of Patents and Trademarks